United States Patent [19]
Yardley et al.

[11] Patent Number: 5,519,025
[45] Date of Patent: May 21, 1996

[54] 4-INDOLYLPIPERAZINYL DERIVATIVES

[75] Inventors: John P. Yardley, King of Prussia; Horace Fletcher, III, Pottstown, both of Pa.

[73] Assignee: American Home Products Corporation, Madison, N.J.

[21] Appl. No.: 419,333

[22] Filed: Apr. 10, 1995

[51] Int. Cl.⁶ .................. C07D 403/04; A61K 31/495
[52] U.S. Cl. ............................. 514/254; 544/373
[58] Field of Search .................. 544/373; 54/254

[56] References Cited

U.S. PATENT DOCUMENTS

| | | | |
|---|---|---|---|
| 4,988,814 | 1/1991 | Abou-Gharbia et al. | 544/295 |
| 5,340,812 | 8/1994 | Cliffe | 514/255 |

*Primary Examiner*—Cecilia Tsang
*Attorney, Agent, or Firm*—Richard K. Jackson

[57] ABSTRACT

This invention provides anxiolytic/antidepressant agents of the formula:

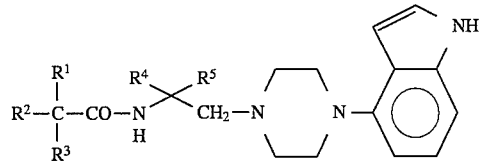

in which
$R^1$ is alkyl;
$R^2$ and $R^3$ are alkyl or taken together they are polymethylene;
$R^4$ is hydrogen or alkyl;
$R^5$ is phenyl, benzyl, substituted phenyl, or substituted benzyl in which the substituents are hydroxy, halo, alkoxy, trifluoromethyl, nitro, cyano, alkoxycarbonyl, amino or dialkylamino;
or a pharmaceutically acceptable salt thereof.

7 Claims, No Drawings

4-INDOLYLPIPERAZINYL DERIVATIVES

BACKGROUND OF THE INVENTION

U.S. Pat. No. 4,988,814 discloses a group of compounds in which the tertiary alkyl carboxylic acid acyl moiety appears. GB 2230781 discloses a group of 5-HT$_{1A}$ antagonists which contain a heteroarylpiperazine moiety.

SUMMARY OF THE INVENTION

In accordance with this invention there is provided a group of novel compounds which exhibit serotonin 5HT$_{1A}$ activity which characterizes them as compounds capable of regulating various physiological functions and behavior including anxiety and affective states. In addition, 5-HT$_1$-like antagonists, like those involved in the present disclosure have been shown to be useful in inhibiting the growth of certain cancers, such as human prostatic carcinoma. Hence, the compounds of this invention are useful in the treatment of cancer. The compounds of the invention are of the following structure:

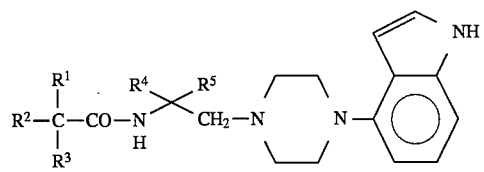

in which

R$^1$ is alkyl of 1 to 6 carbon atoms;

R$^2$ and R$^3$ are alkyl of 1 to 6 carbon atoms or taken together they are polymethylene of 2 to 12 carbon atoms;

R$^4$ is hydrogen or alkyl of 1 to 6 carbon atoms;

R$^5$ is phenyl, benzyl, substituted phenyl, or substituted benzyl in which the substituents are hydroxy, halo, alkoxy of 1 to 6 carbon atoms, trifluoromethyl, nitro, cyano, alkoxycarbonyl of 2 to 7 carbon atoms, amino or dialkylamino in which each alkyl group contains 1 to 6 carbon atoms;

or a pharmaceutically acceptable salt thereof.

The halogen substituent referred to above may be chlorine, bromine, fluorine or iodine, fluorine being preferred. The pharmaceutically acceptable salts are derived from known inorganic or organic acids such as hydrochloric, hydrobromic, sulfuric, nitric, phosphoric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, para-amino benzoic, para-hydroxybenzoic, salicylic, sulfanilic acids, and the like.

The compounds of this invention contain a chiral center, providing for various stereoisomeric forms of the compounds such as racemic mixtures as well as the individual optical isomers, which isomers can be either prepared directly by asymmetric or stereospecific synthesis or by conventional separation of epimers or optical isomers from the racemic mixture.

The preferred compounds are those of the (R) configuration in which R$^1$ is alkyl of 1 to 3 carbon atoms, R$^2$ and R$^3$ are alkyl of 1 to 3 carbon atoms or taken together they are polymethylene of 3 to 7 carbon atoms, R$^4$ is hydrogen and R$^5$ is phenyl or benzyl, or a pharmaceutically acceptable salt thereof.

The compounds of this invention (G) are prepared by a sequence beginning with the reaction of 4-indolyl-piperazine (B) with an N-protected aminoacid (A) in the presence of a coupling reagent such as 1,1'-carbonyldiimidazole, isobutylchloroformate, diethylcyanophosphonate or a carbodiimide, to give the N-protected aminoacid amide (C). The protecting group R$^6$ for the aminoacid is of the urethane type, particularly useful are those in which R$^6$ is tertiary-butyloxycarbonyl (removable by acid) or benzyloxycarbonyl (removable by hydrogenation or by HBr).

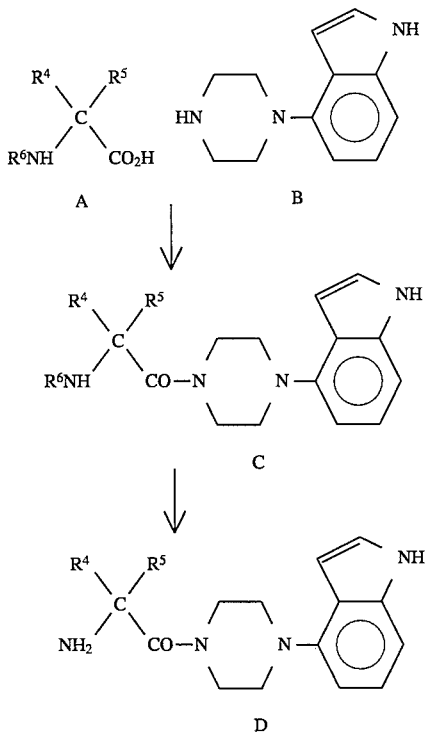

After deprotection of (C) the aminoacid amide may be reduced to (E) using either diborane or LiAlH$_4$.

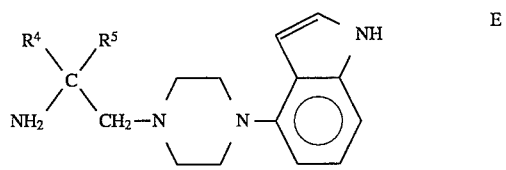

Acylation with a carboxylic acid (F) affords the compounds (G) of the invention.

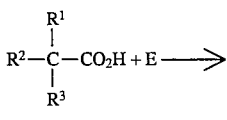

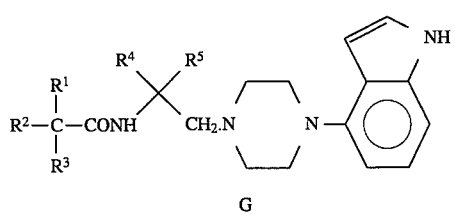

Examples of acylating derivatives include the acid halides (e.g. acid chlorides), azides, anhydrides, imidazolides (e.g.

obtained from carbonyldiimidazole) or o-acylureas (e.g. obtained from a carbodiimide). The compounds of this invention possess high affinity for the serotonin 5-HT$_{1A}$ receptor, and consequently, they are useful as antidepressant and anxiolytic agents for the treatment of a variety of central nervous system disorders such as depression, anxiety, sleep disorders, sexual dysfunction, alcohol and cocaine addiction, cognition enhancement and related problems. In addition, the compounds of this invention show marked selectivity for the 5-HT$_{1A}$ receptors as opposed to the $\alpha_1$ receptors.

High affinity for the serotonin 5-HT$_{1A}$ receptor was established by testing the claimed compound's ability to displace [$^3$H] 8-OHDPAT (dipropylaminotetralin) from the 5-HT$_{1A}$ serotonin receptors in rat hippocampal membrane homogenate following the procedure of B. S. Alexander and M. D. Wood, J. Pharm. Pharmacol. 1988, 40, 888–891. The compound of Example 1, for example, as representative of the other compounds of the invention, exhibited an IC$_{50}$ of 4.33 nM while the (S) isomer in Example 2 exhibited an IC$_{50}$ binding potency at 35.5 nM. Based upon this receptor binding data, the compounds of this invention are characterized as anxiolytic and/or antidepressant agents useful in the treatment of depression and in alleviating anxiety. As such, the compounds may be administered neat or with a pharmaceutical carrier to a patient in need thereof. The pharmaceutical carrier may be solid or liquid.

Applicable solid carders can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carder having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carder can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form. Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from depression or anxiety must be subjectively determined by the attending physician. The variables involved include the specific state of anxiety or depression, and the size, age and response pattern of the patient.

The following examples are presented, without limitation on the scope of the invention claimed hereinafter, to illustrate the preparation of representative members of the compounds of the invention.

EXAMPLE 1

(R)-1-Methyl-cyclohexanecarboxylic acid (2-[4-indolyl]-piperazin-1-yl]- 1-phenyl-ethyl)-amide Benzyloxycarbonyl-D-phenylglycine (2.36 g, 0.0083 mol), and N-methylmorpholine (0.84 g, 0.0083 mol) were stirred in 100 mL of methylene chloride at −15 ° C. under a nitrogen atmosphere as isobutylchloroformate (1.13 g, 0.0083 mol) was added. After 15 minutes, 4-piperazinylindole (1.33 g, 0.0075 mol) was added and the mixture was stirred as it reached room temperature over 20 hours. The solution was washed with water (2×), saturated NaHCO$_3$ (2×) and dried over anhydrous Na$_2$SO$_4$. Evaporation of solvent left 3.6 g of product as a gum which was stirred in 30% HBr in acetic acid (100 mL) at room temperature for 30 minutes. Diethyl ether (300 mL) was added and the hydrobromide salt was filtered., washed with diethyl ether, and dried in vacuo overnight. The salt was shaken in 1N NaOH and the amine was extracted with methylene chloride (3×). The extracts were washed with water, dried over anhydrous Na$_2$SO$_4$, and evaporated to a gum, yield 1.6 g (57.6% from cbz-D-phenylglycine).

(R)(1-Phenylglycyl)-4-(4-indolyl)piperazine (1.6g, 4.92 mmol) and lithium aluminum hydride (0.81 g, 21.7 mmol) were refluxed in THF (500 mL) overnight under nitrogen. The cooled reaction was quenched with 1N NaOH (4.92 mL), stirred for 30 minutes, filtered, and the filtrate was evaporated. The residue was dissolved in ethyl acetate, washed with water, then brine, and dried (Na$_2$SO$_4$). Evaporation of the solvent left (R)-2-(4-indolyl)-piperazin-1-yl-1-phenyl-ethylamine (1.39 g). Yield 88%. The IR spectrum was devoid of carbonyl peaks. Mass spectrum, EI M$^+$.M/H 320.

1-Methylcyclohexanecarbonyl chloride (Beilstein 918, 9II10) prepared from 1-methylcyclohexane-carboxylic acid (0.75 g, 0.0052 mol) and thionyl chloride (0.76 mL, 0.010 mol) was added to a solution of the ethyl amine derivative prepared in the preceding paragraph (1.5 g, 0.0047 mol). Diisopropylethylamine (0.87 mL, 0.005 mol) in 50 mL of methylene chloride was also added. After 2 hours the solution was washed with water, saturated NaHCO$_3$, dried over anhydrous Na$_2$SO$_4$ and evaporated. The product was crystallized from ethyl acetate/hexane. MP 132°–134° C. R$_f$ 0.63 silica, EtOAc/hexane 1:1. IR 1652 cm$^{-1}$. $^1$H NMR (DMSO-d$_6$): δ 1.08 (s, 3H), 1.1–1.5 (m, 10 H), 2.58–2.65 (m, 2H), 2.7–2.78 (m, 2H), 3.0–3.17 (m, 4H), 6.35 (t, 1H), 6.4 (d, 1H), 6.95–6.98 (s, 1H), 6.99–7.02 (d, 1H), 7.19–7.22 (t, 2H), 7.3–7.45 (m, 4H), 7.6–7.64 (d, 1H). The base was converted to the hydrochloride salt in ethyl acetate and precipitated by adding diethyl ether to provide the dihydrochloride, quarter hydrate. MP 206°–208° C. $[\alpha]_D^{25}$ –36.6, c=1% EtOH.

Analytical: $C_{28}H_{36}N_4O_2 \cdot HCl \cdot \tfrac{1}{4} H_2O$. Calc'd: C, 64.42; H, 7.43; N, 10.73; Cl, 13.58. Found: C, 64.37; H, 7.44; N, 10.43; Cl, 13.55.

EXAMPLE 2

(S)-1-Methyl-cyclohexanecarboxylic acid (2-[4-indolyl]-piperazin-1-yl]- 1-phenyl-ethyl)-amide Following the procedure of Example 1, with the exception that benzyloxycarbonyl-L-phenylglycine is employed as the initial reactant provides the title compound as the dihydrochloride, ¼ hydrate. mp—185°–190° C.

Elemental analysis: $C_{28}H_{36}N_4O_2 \cdot HCl \cdot \tfrac{1}{4} H_2O$. Calc'd: C, 64.42; H, 7.43; N, 10.73 Found: C, 64.59; H, 7.78; N, 10.39

EXAMPLE 3

(R)-1-Methyl-cyclohexanecarboxylic acid (2-[4-indolyl]-piperazin-1-yl]- 1-(phenylmethyl)-ethylamide Tert. butoxycarbonyl-D-phenylalanine (2.65g, 0.01 mol) and N-methyl morpholine (1.11 mL, 0.01 mol) were stirred in methylene chloride (150 mL) at −15 ° C. as isobutyl chloroformate (1.3 mL, 0.01 mol) was added dropwise. After 15 minutes, 4-piperazinylindole (2.01 g, 0.01 mol) was added and the mixture was stirred as it reached room temperature over 20 hours. The solution was washed with water, sat. NaHCO₃, dried (anhyd. Na₂SO₄) and evaporated. Yield 4.47 g, 100%. Mass spectrum EI M⁺ 448. The product was stirred in methylene chloride (50 mL) and trifluoroacetic acid (50 mL) at room temperature for 1½ hours and evaporated. The residue was shaken with 1N NaOH and methylene chloride (2×100 mL). The organic layer was washed with water and dried (anhyd. Na₂SO₄). Evaporation of the solvent left the base as an oil. Yield 3.5 g, 100%. Mass spectrum EI M⁺ 348. The base (3.4 g, 0.0097 mol) and lithium aluminum hydride (1.52 g, 0.04 mol) were refluxed in tetrahydrofuran (500 mL) overnight. The cooled reaction was quenched with 1N NaOH (9.1 mL) and filtered. The filtrate was evaporated and the residue was dissolved in ethyl acetate which was washed with water, then brine, dried (anhyd. Na₂SO₄) and evaporated. Yield 3.0 g, 89.7%. Mass spectrum CI (M+H)⁺ 335. The amine (3.0 g, 0.0087 mol), diisopropyl ethyl amine (1.16 g, 0.0087 mol) and 1-methylcyclohexanecarbonyl chloride (1.41 g, 0.0088 mol) were stirred in tetrahydrofuran (100 mL) at room temperature for 72 hours. The solution was evaporated and the residue was shaken with water and ethyl acetate. The ethyl acetate layer was washed with sat. NaHCO₃ then brine and dried (anhyd. Na₂SO₄). Yield 3.05 g, 76.2%. The product was chromatographed on a silica dry column using chloroform/methanol, 99:1 as eluent. Yield 1.5 g. Mass spectrum EI M⁺ 458. The base was converted to dihydrochloride in ethyl acetate with 3.6N HCl in ethyl acetate and dilution with diethyl ether followed by recrystallization from hot ethyl acetate to provide the dihydrochloride, sesquihydrate. IR 1650 cm⁻¹ . ¹H NMR (DMSO-d₆): δ 0.9–0.94 (s, 3H), 1.0–1.37 (m, 10H), 1.8–2.4 (t, 2H), 2.81–2.92 (m, 1H), 295–3.02 (m, 1H), 3.14–3.2 (t, 1H), 3.22–3.45 (m, 8H),3.45–3.55 (d, 1H), 3.57–3.71 (m, 2H), 4.55–4.61 (m, 1H), 6.43 (s, 1H), 6.52–6.55 (d, 1H), 6.95–7.0 (t, 1H), 7.1–7.13 (d, 1H), 7.17–7.2 (dd, 1H), 7.25–7.5 (s, 5H), 7.6–7.65 (d, 1H), 10.8–10.92 (s, 1H), 11.15 (s, 1H).

Analytical: $C_{29}H_{38}N_4O \cdot 2 HCl \cdot 1.5 H_2O$ Calc'd: C, 62.35; H, 7.76; N, 10.03 Found: C,62.31; H, 7.72; N, 9.67

What is claimed is:

1. A compound of the formula:

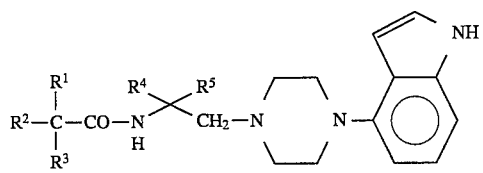

in which

R¹ is alkyl of 1 to 6 carbon atoms;

R² and R³ are alkyl of 1 to 6 carbon atoms or taken together they are polymethylene of 2 to 12 carbon atoms;

R⁴ is hydrogen or alkyl of 1 to 6 carbon atoms;

R⁵ is phenyl, benzyl, substituted phenyl, or substituted benzyl in which the substituents are hydroxy, halo, alkoxy of 1 to 6 carbon atoms, trifluoromethyl, nitro, cyano, alkoxycarbonyl of 2 to 7 carbon atoms, amino or dialkylamino in which each alkyl group contains 1 to 6 carbon atoms;

or a pharmaceutically acceptable salt thereof.

2. A compound of claim 1, of the (R) configuration in which R¹ is alkyl of 1 to 3 carbon atoms, R² and R³ are alkyl of 1 to 3 carbon atoms or taken together they are polymethyleric of 3 to 7 carbon atoms, R⁴ is hydrogen and R⁵ is phenyl or benzyl, or a pharmaceutically acceptable salt thereof.

3. A compound of claim 1 which is 1-methyl-cyclohexanecarboxylic acid [2-[ 4-indolyl]-piperazin- 1-yl]-1-phenyl-ethyl )-amide or a pharmaceutically acceptable salt thereof.

4. The compound of claim 1 which is (R)-1-methylcyclohexanecarboxylic acid (2-[4-indolyl]-piperazin-1-yl]-1-phenyl-ethyl)-amide or a pharmaceutically acceptable salt thereof.

5. The compound of claim 1 which is (S)-1-methyl-cyclohexanecarboxylic acid [2-[4-indolyl]-piperazin-1-yl]-1-phenyl-ethyl)-amide or a pharmaceutically acceptable salt thereof.

6. A compound of claim 1 which is 1-methyl-cyclohexanecarboxylic acid [2-[4-indolyl]-piperazin-1-yl]-1-(phenylmethyl)-ethylamide or a pharmaceutically acceptable salt thereof.

7. The compound of claim 1 which is (R)-1-methylcyclohexanecarboxylic acid [2-[4-indolyl]-piperazin-1-yl]-1-(phenylmethyl)-ethylamide or a pharmaceutically acceptable salt thereof.

* * * * *